(12) United States Patent
Zimmerman

(10) Patent No.: US 7,179,824 B2
(45) Date of Patent: Feb. 20, 2007

(54) ARTHROPODICIDAL ANTHRANILAMIDES

(75) Inventor: William Thomas Zimmerman, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 281 days.

(21) Appl. No.: 10/485,093

(22) PCT Filed: Sep. 6, 2002

(86) PCT No.: PCT/US02/28274

§ 371 (c)(1), (2), (4) Date: Jan. 26, 2004

(87) PCT Pub. No.: WO03/027099

PCT Pub. Date: Apr. 3, 2003

(65) Prior Publication Data

US 2004/0186141 A1 Sep. 23, 2004

Related U.S. Application Data

(60) Provisional application No. 60/324,011, filed on Sep. 21, 2001.

(51) Int. Cl.
- A01N 43/56 (2006.01)
- A01N 43/40 (2006.01)
- C07D 401/12 (2006.01)

(52) U.S. Cl. .............. 514/341; 546/276.1; 546/275.4

(58) Field of Classification Search ............ 546/276.1, 546/275.4; 514/341
See application file for complete search history.

(56) References Cited

U.S. PATENT DOCUMENTS

| 4,321,371 A | 3/1982 | Parg et al. |
| 5,474,998 A | 12/1995 | Harrison et al. |
| 5,602,126 A | 2/1997 | Barnette et al. |
| 5,728,693 A | 3/1998 | Stevenson |

FOREIGN PATENT DOCUMENTS

| DE | 4428380 A | 8/1994 |
| DE | 19840322 A1 | 9/1998 |
| EP | 0919542 A2 | 6/1999 |
| EP | 1193254 A1 | 1/2001 |
| NL | 9202078 A | 11/1992 |
| WO | WO 92/12133 | 7/1992 |
| WO | WO 96/38419 | 12/1996 |
| WO | WO 01/02354 A1 | 1/2001 |
| WO | WO 01/32628 A1 | 5/2001 |
| WO | WO 01/70671 A2 | 9/2001 |

OTHER PUBLICATIONS

XP002177117 Suto, Mark J. et al.: Tetrahedron Letters, vol. 36, No. 40, 1995, pp. 7213-7216, Elsevier Science Publishers, Amsterdam, NL.
Klaubert et al., J.Med.Chem., vol. 24, No. 6, pp. 748-752, 1981.

*Primary Examiner*—Patricia L. Morris

(57) ABSTRACT

This invention pertains to a compound of Formula I, its N-oxide or an agriculturally suitable salt of the compound (Formula I) wherein $R^1$, $R^2$, $R^3$, $R^4$, and $R^5$ are as defined in the disclosure. Also disclosed are methods for controlling arthropods comprising contacting the arthropods or their environment with an arthropodicially effective amount of a compound for Formula I; and compositions containing the compounds of Formula I

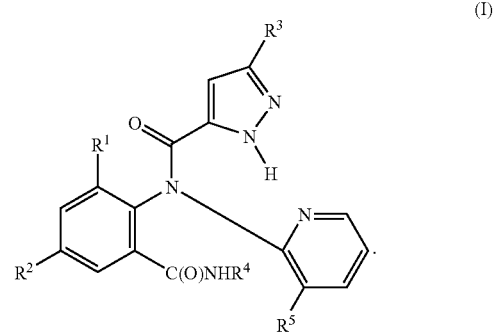

6 Claims, No Drawings

ARTHROPODICIDAL ANTHRANILAMIDES

FIELD OF THE INVENTION

This invention relates to certain anthranilamides, their N-oxides, agriculturally suitable salts and compositions, and methods of their use as arthropodicides in both agronomic and nonagronomic environments.

BACKGROUND OF THE INVENTION

The control of arthropod pests is extremely important in achieving high crop efficiency. Arthropod damage to growing and stored agronomic crops can cause significant reduction in productivity and thereby result in increased costs to the consumer. The control of arthropod pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

NL 9202078 discloses N-acyl anthranilic acid derivatives of Formula i as insecticides

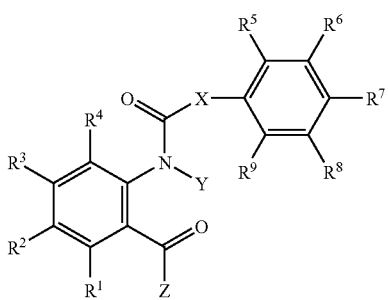

wherein, inter alia,
X is a direct bond;
Y is H or $C_1$–$C_6$ alkyl;
Z is $NH_2$, $NH(C_1$–$C_3$ alkyl) or $N(C_1$–$C_3$ alkyl)$_2$; and
$R^1$ through $R^9$ are independently H, halogen, $C_1$–$C_6$ alkyl, phenyl, hydroxy, $C_1$–$C_6$ alkoxy or $C_1$–$C_7$ acyloxy.

SUMMARY OF THE INVENTION

This invention pertains to a compound of Formula I, its N-oxide or an agriculturally suitable salt of the compound

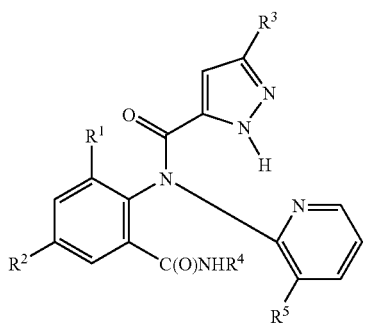

wherein
$R^1$ and $R^2$ are each independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, or $C_3$–$C_6$ trialkylsilyl;
$R^3$ is H, $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl;
$R^4$ is H; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, phenyl, phenoxy, 5-membered heteroaromatic rings, and 6-membered heteroaromatic rings; each phenyl, phenoxy, 5-membered heteroaromatic ring, and 6-membered heteroaromatic ring optionally substituted with from one to three substituents independently selected from $R^7$;
$R^5$ is H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, or $C_3$–$C_6$ trialkylsilyl; and
each $R^7$ is $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

This invention also pertains to a method for controlling arthropods comprising contacting the arthropods or their environment with an arthropodicidally effective amount of a compound of Formula I.

This invention also pertains to arthropodicidal compositions comprising an arthropodicidally effective amount of a compound of Formula I and at least one additional component selected from the group consisting of surfactants, solid diluents and liquid diluents.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4- hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyclobutyl, cyclopentyl and cyclohexyl.

The term "heterocyclic ring" or heterocyclic ring system" denotes rings or ring systems in which at least one ring atom is not carbon and comprises 1 to 4 heteroatoms independently selected from the group consisting of nitrogen, oxygen and sulfur, provided that each heterocyclic ring contains no more than 4 nitrogens, no more than 2 oxygens and no more than 2 sulfurs. The heterocyclic ring can be attached through any available carbon or nitrogen by replacement of hydrogen on said carbon or nitrogen. The term "aromatic ring system" denotes fully unsaturated carbocycles and heterocycles in which the polycyclic ring system is aromatic (where aromatic indicates that the Hückel rule is satisfied for the ring system). The term "heteroaromatic ring" denotes fully aromatic rings in which at least one ring atom is not carbon and comprises 1 to 4 heteroatoms independently selected from the group consisting of nitrogen, oxygen and sulfur, provided that each heterocyclic ring contains no more than 4 nitrogens, no more than 2 oxygens and no more than 2 sulfurs (where aromatic indicates that the Hückel rule is satisfied). The heterocyclic ring can be attached through any available carbon or nitrogen by replacement of hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or filly substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$.

The total number of carbon atoms in a substituent group is indicated by the "$C_{i-Cj}$" prefix where i and j are numbers from 1 to 8. For example, $C_1$–$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula I comprises a heterocyclic ring, all substituents are attached to this ring through any available carbon or nitrogen by replacement of a hydrogen on said carbon or nitrogen.

The term "optionally substituted with one to three substituents" indicates that one to three of the available positions on the group may be substituted. When a group contains a substituent which can be hydrogen, for example $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof The compounds of the invention may be present as a mixture of stereoisomers, individual stereoisomers, or as an optically active form.

Compounds of this invention can exist as one or more tautomers. In particular, compounds of Formula I can also exist as Formula Ia. One skilled in the art will appreciate that the tautomeric forms I and Ia are in equilibrium and thus are biological equivalents and that one tautomer may predominate over the other under various conditions. Accordingly, the present invention comprises compounds selected from Formula I or Ia, and N-oxides and agriculturally suitable salts thereof. The compounds of the invention may be present as a mixture of tautomers or as individual tautomers. Reference to Formula I herein encompasses Formula I and its tautomers such as Formula Ia.

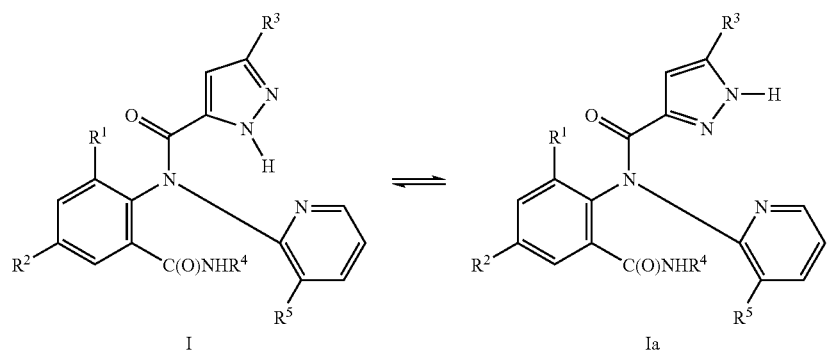

One skilled in the art will appreciate that not all nitrogen-containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocylic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Preferred for ease of synthesis, cost and/or biological efficacy are:

Preferred 1. Compounds of Formula I wherein
  $R^1$ is $C_1$–$C_3$ alkyl, $CF_3$, $OCF_3$, $OCHF_2$, $S(O)_pCF_3$, $S(O)_pCHF_2$ or halogen;
  $R^2$ is H, halogen, $C_1$–$C_3$ alkyl or $C_1$–$C_3$ haloalkyl;
  $R^3$ is halogen or $CF_3$;
  $R^4$ is $C_1$–$C_4$ alkyl optionally substituted with halogen, CN, $OCH_3$, or $S(O)_pCH_3$;
  $R^5$ is halogen, $C_1$–$C_4$ alkyl, $C_1$–$C_4$ haloalkyl or $C_1$–$C_4$ haloalkoxy; and
  p is 0, 1 or 2.

Preferred 2. Compounds of Preferred 1 wherein
  $R^1$ is $CH_3$, Cl or Br;
  $R^2$ is H, F, Cl, Br, I or $CF_3$;
  $R^3$ is $CF_3$, Cl or Br;
  $R^4$ is $C_2$$C_4$ alkyl; and
  $R^5$ is Cl or Br.

Specifically preferred is the compound N-(3-chloro-2-pyridinyl)-N-[2-methyl-6-[[(1-methylethyl)amino]carbonyl]phenyl]-5-(trifluoromethyl)-1H-pyrazole-3-carboxamide. Also specifically preferred are the compounds 3-bromo-N-(4-chloro-2-methyl)-6-[[(1-methylethyl)amino]carbonyl]phenyl]-N-(3-chloro-2-pyridinyl)-1H-pyrazole-5-carboxamide and N-[4-chloro-2-methyl -6-[[(1-methylethyl)amino]carbonyl]phenyl]-N-(3-chloro-2-pyridinyl)-3-(trifluoromethyl)-1H-pyrazole-5-carboxamide.

This invention also relates to arthropodicidal compositions comprising arthropodicidally effective amounts of the compounds of the invention and at least one of a surfactant, a solid diluent or a liquid diluent. The preferred compositions of the present invention are those which comprise the above preferred compounds.

This invention also relates to a method for controlling arthropods comprising contacting the arthropods or their environment with an arthropodicidally effective amount of the compounds of the invention (e.g., as a composition described herein). The preferred methods of use are those involving the above preferred compounds.

Of note are compounds of Formula II or III, their N-oxides or agriculturally suitable salts

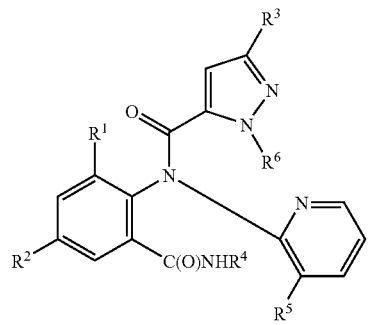

II

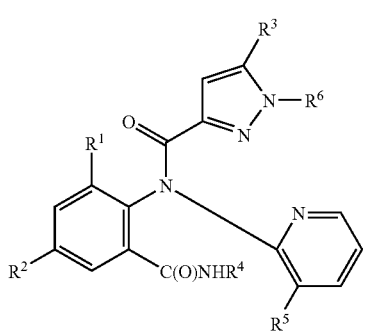

III wherein
  $R^1$, $R^2$, $R^3$, $R^4$, $R^5$ and $R^7$ are defined as above for Formula I; and
  $R^6$ is a group that is labile under physiological conditions to provide a compound of Formula I (i.e. wherein $R^6$ is H).

Examples of $R^6$ groups that are labile under physiological conditions to provide a compound of Formula I (i.e. wherein $R^6$ is H) include $C_1$–$C_4$ alkyl, hydroxymethyl, $C_2$–$C_6$ alkoxyalkyl, $C_1$–$C_4$ alkylsulfonyl, $C_1$–$C_4$ haloalkylsulfonyl, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, $C_3$–$C_6$ trialkylsilyl; and benzoyl or phenylsulfonyl, each optionally substituted with one to three substituents independently selected from $R^7$. These groups can be cleaved from compounds of Formula II or III to provide a compound of Formula I by various nucleophilic displacements, hydrolytic processes or enzymatically-facilitated processes.

The compounds of Formula I can be prepared by one or more of the following methods and variations as described in Schemes 1–14. The definitions of $R^1$, $R^2$, $R^3$, $R^4$ and $R^5$ in the compounds of Formulae 1–25 below are as defined above in the Summary of the Invention unless indicated otherwise.

Compounds of Formula I can be prepared by the reaction of anthranilamides of Formula IV with various bases as outlined in Scheme 1. This type of rearrangement reaction is analogous to the known base-induced Smiles rearrangement, which has been well documented in the literature. For the reviews of Smiles rearrangement, see J. F. Bunnett, R. E. Zahler, *Chem. Revs.* 1951, 49, 362 and W. E. Truce, et. al., *Organic Reactions* 1970, 18, 99. Generally, an equilibrium is established between IV and I to varying proportions depending on the choice of base and solvent, and the components can be separated by typical chromatographic methods. The reaction can be run neat or in a variety of suitable solvents including acetonitrile, tetrahydrofuran, diethyl ether, dichloromethane and chloroform with optimum temperatures ranging from room temperature to the reflux temperature of the solvent. Bases used in this transformation include strong amine bases such as 1,8-diazabicyclo[5.4.0]undec-7-ene, 1,1,3,3-tetramethylguanidine and the like, tertiary amine bases, and alkali metal hydrides and alkoxides. Preferably, $R^4$ is $C_2$–$C_4$ alkyl for this rearrangement process.

-continued

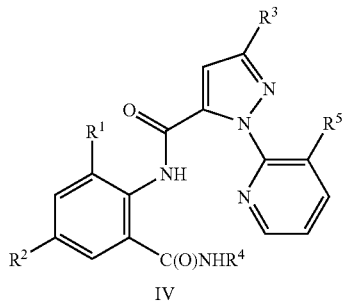

IV

Scheme 1

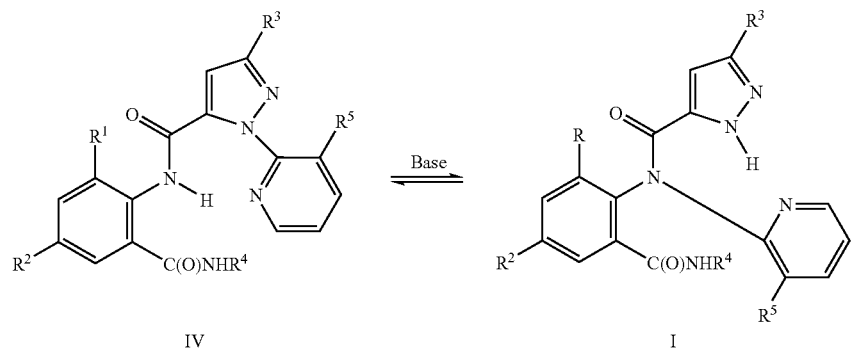

IV           I

Compounds of Formula II or Formula III (wherein $R^6$ is other than hydrogen) are typically prepared by reaction of a compound of Formula I with the appropriate acylating or alkylating agent, typically in the presence of a base as an acid scavenger.

Compounds of Formula IV can be prepared by the reaction of benzoxazinones of Formula 2 with $C_1$–$C_4$ alkyl amines as outlined in Scheme 2. The reaction can be run neat or in a variety of suitable solvents including tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095–2103 and references cited within. See also Coppola, *J. Heterocyclic Chemistry* 1999, 36, 563–588.

Scheme 2

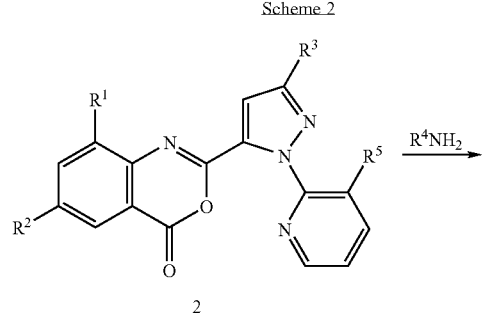

2

Benzoxazinones of Formula 2 can be prepared by a variety of procedures. Two procedures that are especially useful are detailed in Schemes 3–4. In Scheme 3, a benzoxazinone of Formula 2 is prepared directly via coupling of a pyrazolecarboxylic acid of Formula 4 with an anthranilic acid of Formula 3. This involves sequential addition of methanesulfonyl chloride in the presence of a tertiary amine such as triethylamine or pyridine to a pyrazolecarboxylic acid of Formula 4, followed by the addition of an anthranilic acid of Formula 3, followed by a second addition of tertiary amine and methanesulfonyl chloride. This procedure generally affords good yields of the benzoxazinone.

Scheme 3

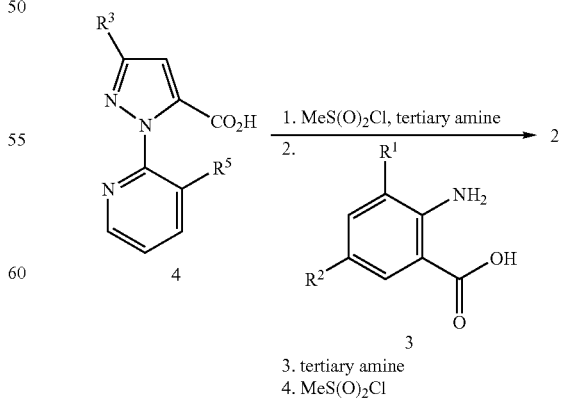

3. tertiary amine
4. MeS(O)$_2$Cl

Scheme 4 depicts an alternate preparation for benzoxazinones of Formula 2 involving coupling of a pyrazole acid chloride of Formula 6 with an isatoic anhydride of Formula 5 to provide the Formula 2 benzoxazinone directly. Solvents such as pyridine or pyridine/acetonitrile are suitable for this reaction. The acid chlorides of Formula 6 are available from the corresponding acids of Formula 4 by known procedures such as chlorination with thionyl chloride or oxalyl chloride. This procedure generally affords good yields of the benzoxazinone and is illustrated with greater detail in Example 1.

Scheme 4

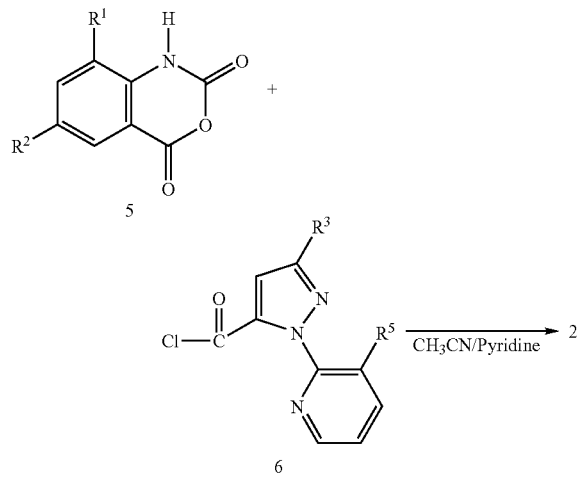

Anthranilic acids of Formula 3 are available by a variety of known methods. Many of these compounds are known. As shown in Scheme 5, anthranilic acids containing an $R^2$ substituent of chloro, bromo or iodo can be prepared by direct halogenation of an unsubstituted anthranilic acid of Formula 7 with N-chlorosuccinimide (NCS), N-bromosuccinimide (NBS) or N-iodosuccinimide (NIS) respectively in solvents such as N,N-dimethylformamide (DMF) to produce the corresponding substituted acid of Formula 3.

Scheme 5

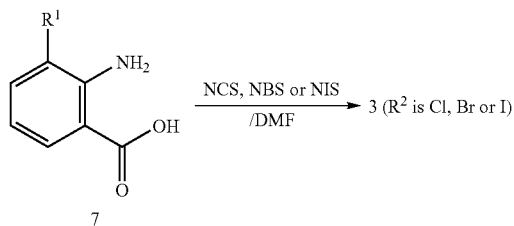

Preparation of the isatoic anhydrides of Formula 5 can be achieved from isatins of Formula 9 as outlined in Scheme 6. Isatins of Formula 9 are available from aniline derivatives of Formula 8 following literature procedures. Oxidation of isatin 9 with hydrogen peroxide generally affords good yields of the corresponding isatoic anhydride 5 (*Angew. Chem. Int. Ed. Engl.* 1980, 19, 222–223). Isatoic anhydrides 5 are also available from the anthranilic acids 3 via many known procedures involving reaction of 3 with phosgene or a phosgene equivalent.

Scheme 6

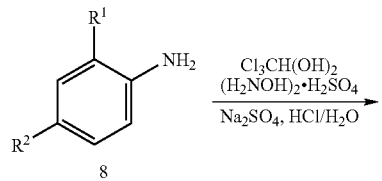

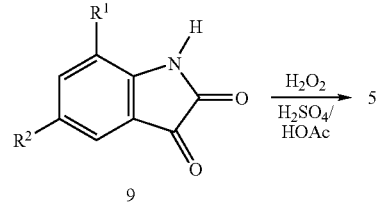

Pyrazolecarboxylic acids of Formula 4 can be prepared by procedures outlined in Scheme 7. Reaction of a pyrazole of Formula 10 with a 2,3-dihalopyridine of Formula 11 affords good yields of the 1-pyridylpyrazole 12 with good specificity for the desired regiochemistry. Metallation of 12 with lithium diisopropylamide (LDA) followed by quenching of the lithium salt with carbon dioxide affords the pyrazolecarboxylic acid of Formula 4. Additional details for these procedures are provided in Example 1.

Scheme 7

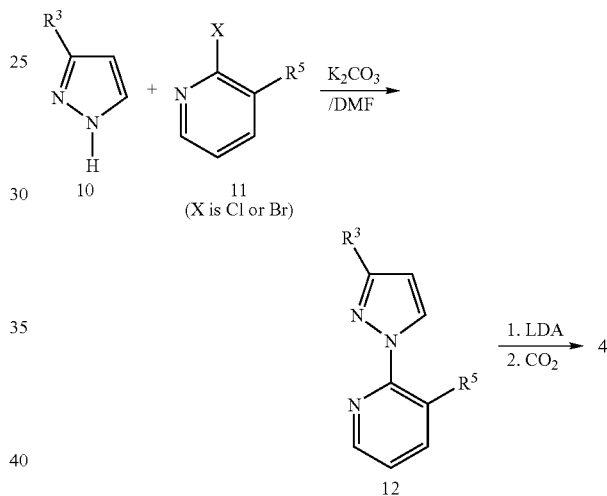

The starting pyrazoles of Formula 10 wherein $R^3$ is $CF_3$, Cl or Br are known compounds or can be prepared by known methods. The pyrazole of Formula 10 wherein $R^3$ is $CF_3$ can be prepared by literature procedures (*J. Fluorine Chem.* 1991, 53(1), 61–70). Pyrazoles of Formula 10 wherein $R^3$ is Cl or Br can be prepared by literature procedures (*Chem. Ber.* 1966, 99(10), 3350–7). A useful alternative method for the preparation of 10 wherein $R^3$ is Cl or Br is depicted in Scheme 8.

Scheme 8

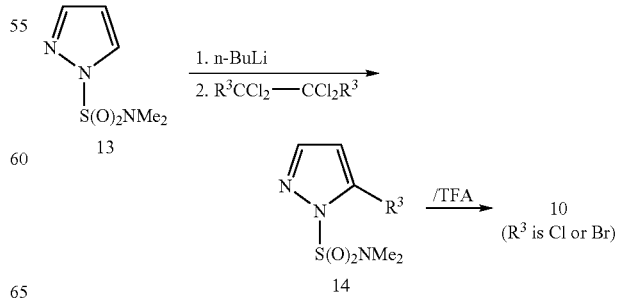

Metallation of the sulfamoyl pyrazole 13 with n-butyllithium followed by direct halogenation of the anion with either hexachloroethane (for $R^3$ being Cl) or 1,2-dibromotetrachloroethane (for $R^3$ being Br) affords the halogenated derivatives 14. Removal of the sulfamoyl group with trifluoroacetic acid (TFA) at room temperature proceeds cleanly and in good yield to afford the pyrazoles 10 wherein $R^3$ is Cl or Br respectively.

As an alternative to the method illustrated in Scheme 7, pyrazolecarboxylic acids of Formula 4 wherein $R^3$ is $CF_3$ can also be prepared by the method outlined in Scheme 9.

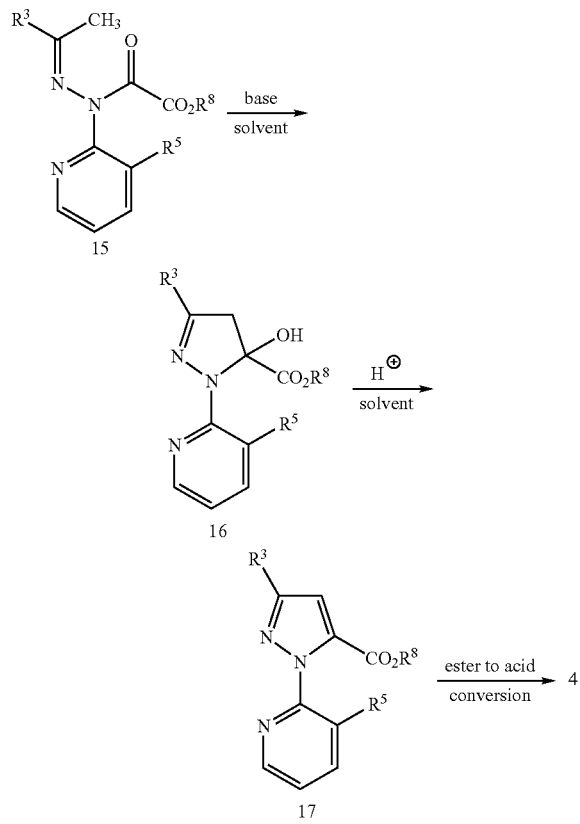

Reaction of a compound of Formula 15 wherein $R^8$ is $C_1$–$C_4$ alkyl with a suitable base in a suitable organic solvent affords the cyclized product of Formula 16 after neutralization with an acid such as acetic acid. The suitable base can be, for example but not limitation, sodium hydride, potassium t-butoxide, dimsyl sodium ($CH_3S(O)CH_2Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride.

Dehydration of the compound of Formula 16 to give the compound of Formula 17, followed by converting the carboxylic ester function to carboxylic acid, affords the compound of Formula 4. The dehydration is effected by treatment with a catalytic amount of a suitable acid. This catalytic acid can be, for example but not limitation, sulfuric acid. The reaction is generally conducted using an organic solvent. As one skilled in the art will realize, dehydration reactions may be conducted in a wide variety of solvents in a temperature range generally between about 0 and 200° C., more preferably between about 0 and 100° C.). For the dehydration in the method of Scheme 9, a solvent comprising acetic acid and temperatures of about 65° C. are preferred. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp. 224–269 for a review of methods). For the method of Scheme 9, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 4. The carboxylic acid can be isolated by methods known to those skilled in the art, including crystallization, extraction and distillation.

Compounds of Formula 15 can be prepared by the method outlined in Scheme 10.

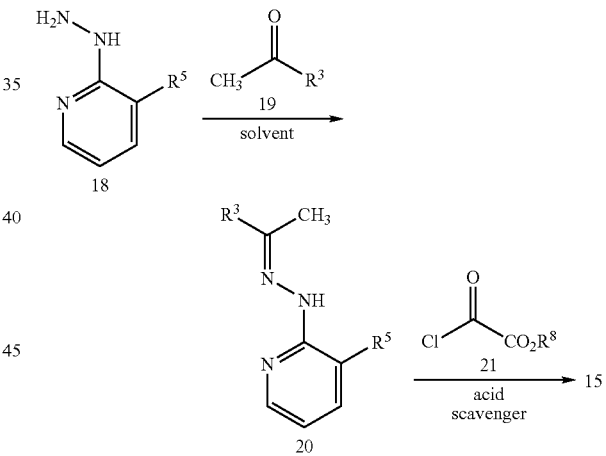

wherein $R^3$ is $CF_3$ and $R^8$ is $C_1$–$C_4$ alkyl.

Treatment of a hydrazine compound of Formula 18 with a ketone of Formula 19 in a solvent such as water, methanol or acetic acid gives the hydrazone of Formula 20. One skilled in the art will recognize that this reaction may require catalysis by an optional acid and may also require elevated temperatures depending on the molecular substitution pattern of the hydrazone of Formula 20. Reaction of the hydrazone of Formula 20 with the compound of Formula 21 in a suitable organic solvent such as, for example but not limitation, dichloromethane or tetrahydrofuran in the presence of an acid scavenger such as triethylamine provides the compound of Formula 15. The reaction is usually conducted at a temperature between about 0 and 100 ° C. Further experimental details for the method of Scheme 10 are illustrated in Example 2. Hydrazine compounds of Formula 18 can be prepared by standard methods, such as by contacting the corresponding halo compound of Formula 11 with hydrazine.

As an alternative to the method illustrated in Scheme 7, pyrazolecarboxylic acids of Formula 4 wherein $R^3$ is Cl or Br can also be prepared by the method outlined in Scheme 11.

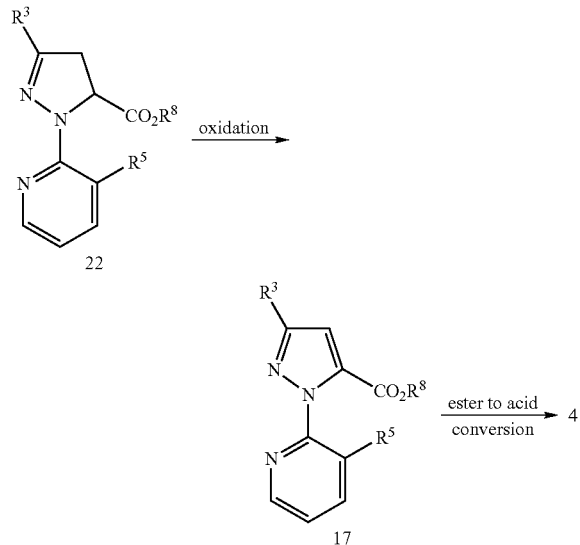

wherein $R^8$ is $C_1$–$C_4$ alkyl.

Oxidization of the compound of Formula 22 optionally in the presence of acid to give the compound of Formula 17 followed by conversion of the carboxylic ester function to the carboxylic acid provides the compound of Formula 4. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 22 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 22. To obtain complete conversion, one to five equivalents of acid can be used. The preferred oxidant is potassium persulfate and the oxidation is preferably carried out in the presence of sulfuric acid. The reaction can be carried out by mixing the compound of Formula 22 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 17 can be isolated by methods known to those skilled in the art, including crystallization, extraction and distillation. Methods suitable for converting the ester of Formula 17 to the carboxylic acid of Formula 4 are already described for Scheme 9.

Compounds of Formula 22 can be prepared from corresponding compounds of Formula 23 as shown in Scheme 12.

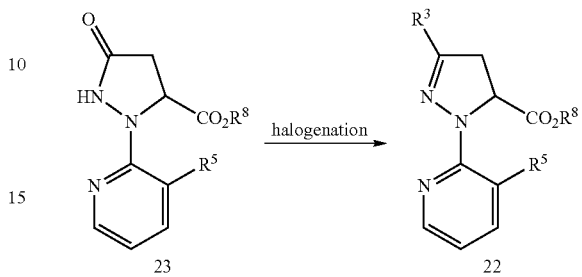

wherein $R^8$ is $C_1$–$C_4$ alkyl.

Treatment of a compound of Formula 23 with a halogenating reagent, usually in the presence of a solvent, affords the corresponding halo compound of Formula 22. Halogenating reagents that can be used include phosphorus oxyhalides, phosphorus trihalides, phosphorus pentahalides, thionyl chloride, dihalotrialkylphophoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 23 should be used, preferably between about 0.33 and 1.2 equivalents. To obtain complete conversion, at least 0.20 equivalents of phosphorus pentahalide versus the compound of Formula 23 should be used, preferably between about 0.20 and 1.0 equivalents. Compounds of Formula 23 wherein $R^8$ is $C_1$–$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 23 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 22, can be isolated by methods known to those skilled in the art, including crystallization, extraction and distillation.

Alternatively, compounds of Formula 22 wherein $R^3$ is Br or Cl can be prepared by treating the corresponding compounds of Formula 22 wherein $R^3$ is a different halogen (e.g., Cl for making Formula 22 wherein $R^3$ is Br) or a sulfonate group such as p-toluenesulfonate, benzenesulfonate and methanesulfonate with hydrogen bromide or hydrogen chloride, respectively. By this method the $R^3$ halogen or sulfonate substituent on the Formula 22 starting compound is replaced with Br or Cl from hydrogen bromide or hydrogen chloride, respectively. The reaction is conducted in a suitable solvent such as dibromomethane, dichloromethane or acetonitrile. The reaction can be conducted at or near atmospheric pressure or above atmospheric pressure in a pressure vessel. When $R^3$ in the starting compound of Formula 22 is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30 ° C. Addition of a Lewis acid catalyst (such as aluminum tribromide for preparing Formula 22 wherein $R^3$ is Br) can facilitate the reaction. The product of Formula 22 is isolated by the usual methods known to those skilled in the art, including extraction, distillation and crystallization.

Starting compounds of Formula 22 wherein $R^3$ is Cl or Br can be prepared from corresponding compounds of Formula 23 as already described. Starting compounds of Formula 22 wherein $R^3$ is a sulfonate group can likewise be prepared from corresponding compounds of Formula 23 by standard methods such as treatment with a sulfonyl chloride (e.g., p-toluenesulfonyl chloride) and base such as a tertiary amine (e.g., triethylamine) in a suitable solvent such as dichloromethane.

As an alternative to the method illustrated in Scheme 7, pyrazolecarboxylic acids of Formula 4 wherein $R^3$ is $OCH_2CF_3$ can also be prepared by the method outlined in Scheme 13.

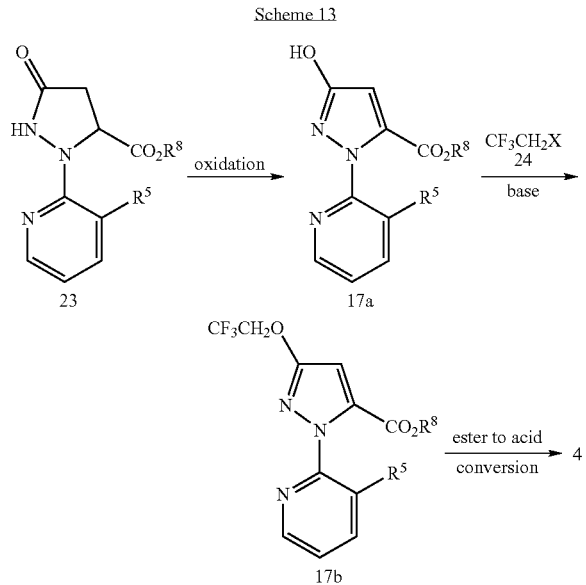

wherein $R^8$ is $C_1$–$C_4$ alkyl, and X is a leaving group.

In this method, instead of being halogenated as shown in Scheme 12, the compound of Formula 23 is oxidized to the compound of Formula 17a. The reaction conditions for this oxidation are as already described for the conversion of the compound of Formula 22 to the compound of Formula 17 in Scheme 11.

The compound of Formula 17a is then alkylated to form the compound of Formula 17b by contact with an alkylating agent $CF_3CH_2X$ (24) in the presence of a base. In the alkylating agent 24, X is a nucleophilic reaction leaving group such as halogen (e.g., Br, I), $OS(O)_2CH_3$ (methanesulfonate), $OS(O)_2CF_3$, $OS(O)_2Ph$-p-$CH_3$ (p-toluenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo[5.4.0]undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, such as such as acetonitrile, N,N-dimethylformamide, and the like. Alcohols and polar aprotic solvents are preferred for use with inorganic bases. Potassium carbonate as base and acetonitrile as solvent are preferred. The reaction is generally conducted between about 0 and 150° C., with most typically between ambient temperature and 100° C. The product of Formula 17b can be isolated by conventional techniques such as extraction. The ester of Formula 17b can then be converted to the carboxylic acid of Formula 4 by the methods already described for the conversion of Formula 17 to Formula 4 in Scheme 9.

Compounds of Formula 23 can be prepared from compounds of Formula 18 as outlined in Scheme 14.

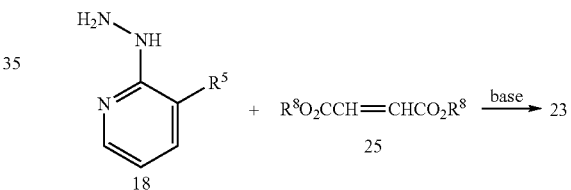

wherein $R^8$ is $C_1$–$C_4$ alkyl.

In this method, a hydrazine compound of Formula 18 is contacted with a compound of Formula 25 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 18 should be used, preferably between 0.9 and 1.3 equivalents. Greater than 1.0 equivalents of the compound of Formula 25 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 18 and the base in the solvent. The mixture can be heated or cooled to a desired temperature and the compound of Formula 25 added over a period of time. Typically reaction temperatures are between 0° C. and the boiling point of the solvent used. The reaction may be conducted under greater than atmospheric pressure in order to increase the boiling point of the solvent. Temperatures between about 30 and 90 ° C. are generally preferred. The addition time can be as quick as heat transfer allows. Typical addition times are between 1 minute and 2 hours. Optimum reaction temperature and addition time vary depending upon the identities of the compounds of Formula 18 and Formula 25. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —$CO_2R^8$ function on the compound of Formula 23 may be hydrolyzed to —$CO_2H$; for example, the presence of water in the reaction mixture can promote such hydrolysis. If the carboxylic acid (—$CO_2H$) is formed, it can be converted back to —$CO_2R^8$ wherein $R^8$ is $C_1$–$C_4$ alkyl using esterification methods well-known in the art. The desired product, a compound of Formula 23, can; be isolated by methods known to those skilled in the art, such as crystallization, extraction or distillation.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

It is believed that one skilled in the art using the preceding description can utilize the present invention to its fullest extent. The following Example is, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s means singlet, d means doublet, t means triplet, q means quartet, m means multiplet, dd means doublet of doublets, dt means doublet of triplets, br s means broad singlet.

EXAMPLE 1

Preparation of N-(3-chloro-2-pyridinyl)-N-[2-methyl-6-[[(1-methylethyl)amino]carbonyl]phenyl]-5-(trifluoromethyl)-1H-pyrazole-3-carboxamide Step A: Preparation of 3-chloro-2-[3-(trifluoromethyl)-1H-pyrazol-1-yl]pyridine To a mixture of 2,3-dichloropyridine (99.0 g, 0.67 mol) and 3-trifluoromethyl pyrazole (83 g, 0.61 mol) in dry N,N-dimethylformamide (300 mL) was added potassium carbonate (166.0 g, 1.2 mol) and the reaction was then heated to 110–125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139–141° C., 7 mm) afforded the desired intermediate as a clear yellow oil (113.4 g).

$^1$H NMR (CDCl$_3$) δ 6.78 (s,1H), 7.36 (t,1H), 7.93 (d,1H), 8.15 (s,1H), 8.45 (d,1H).

Step B: Preparation of 1-(3-chloro-2-pyridinyl-3-(trifluoromethyl)-1H-pyrazole-5-carboxylic acid To a solution of 3-chloro-2-[3-(trifluoromethyl)-1H-pyrazol-1-yl]pyridine (i.e. the product from Step A) (105.0 g, 425 mmol) in dry tetrahydrofuran (700 mL) at −75° C. was added via cannula a −30° C. solution of lithium diisopropylamide (425 mmol) in dry tetrahydrofuran (300 mL). The deep red solution was stirred for 15 minutes, after which time carbon dioxide was bubbled rough at −63° C. until the solution became pale yellow and the exothermicity ceased. The reaction was stirred for an additional 20 minutes and then quenched with water (20 mL). The solvent was removed under reduced pressure, and the reaction mixture partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously, and additional acid was added to lower the pH to 2.5–3. The orange oil congealed into a granular solid, which was filtered, washed successively with water and 1N hydrochloric acid, and dried under vacuum at 50° C. to afford the title product as an off-white solid (130 g). (Product from another run following similar procedures melted at 175–176° C.)

$^1$H NMR (DMSO-d$_6$) δ 7.61 (s,1H), 7.76 (dd,1H), 8.31 (d,1H), 8.60 (d,1H).

Step C: Preparation of 8-methyl-2H-3,1-benzoxazine-2,4(1H)-dione

To a solution of 2-amino-3-methylbenzoic acid (6 g) in dry 1,4-dioxane (50 mL) was added dropwise a solution of trichloromethyl chloroformate (8 mL) in dry 1,4-dioxane (25 mL), with ice-water cooling to keep the reaction temperature below 25° C. A white precipitate began to form during the addition. The reaction mixture was stirred at room temperature overnight. The precipitated solids were removed by filtration and washed with 1,4-dioxane (2×20 mL) and hexane (2×15 mL) and air-dried to yield 6.51 g of off-white solid.

$^1$H NMR (DMSO-d$_6$) δ 2.33 (s,3H), 7.18 (t,1H), 7.59 (d,1H), 7.78 (d,1H), 11.0 (br s,1H).

Step D: Preparation of 2-[1-(3-chloro-2-pyridinyl)-3-(trifluoromethyl)-1H-pyrazol-5-yl]-8-methyl-4H-3,1-benzoxazin-4-one To a suspension of 1-(3-chloro-2-pyridinyl)-3-(trifluoromethyl)-1H-pyrazole-5-carboxylic acid (the product from Step B) (146 g, 500 mmol) in dichloromethane (approximately 2 L) was added N,N-dimethylformamide (20 drops) and oxalyl chloride (67 mL, 750 mmol) in approximately 5-mL portions over approximately 2 h. Vigorous gas evolution occurred during the addition. The reaction mixture was stirred at room temperature overnight. The reaction mixture was concentrated in vacuo to provide the crude acid chloride as an opaque orange mixture. This material was taken up in dichloromethane, filtered to remove some solids and the reconcentrated and used without further purification. The crude acid chloride was dissolved in acetonitrile (250 mL) and added to a suspension of the product from Step C in acetonitrile (400 mL). Pyridine (250 mL) was added, the mixture was stirred for 15 min at room temperature, then warmed to reflux for 3 h. The resulting mixture was cooled to room temperature and stirred overnight to provide a solid mass. Additional acetonitrile was added and the mixture was mixed to form a thick slurry. The solids were collected and washed with cold acetonitrile. The solids were air-dried and the dried in vacuo at 90° C. for 5 h to yield 144.8 g of fluffy white solid.

$^1$H NMR (CDCl$_3$) δ 1.84 (s,3H), 7.4 (t, 1H), 7.6 (m,3H), 8.0 (dd,1H), 8.1 (s,1H), 8.6 (d,1H).

Step E: Preparation of 1-(3-chloro-2-pyridinyl)-N-[2-methyl-6-[[(1-methylethyl)amino]carbonyl]phenyl]-3-(trifluoromethyl)-1H-pyrazole-5-carboxamide To a suspension of 2-[1-(3-chloro-2-pyridinyl)-3-(trifluoromethyl)-1H-pyrazol-5-yl]-8-methyl-4H-3,1-benzoxazin-4-one (the product from Step D) (124 g, 300 mmol) in dichloromethane (500 mL) was added dropwise isopropylamine (76 mL, 900 mmol) at room temperature. The temperature of the reaction mixture rose and the suspension thinned during the addition. The reaction mixture was then warmed to reflux for 1.5 h. A new suspension formed. The reaction mixture was cooled to room temperature and diethyl ether (1.3 L) was added and the mixture stirred at room temperature overnight. The solids were collected and washed with ether. The solids were air-dried and the dried in vacuo at 90° C. for 5 h to yield 122 g of the title compound as a fluffy white solid, melting at 194–196° C.

Step F: Preparation of N-(3-chloro-2-pyridinyl)-N-[2-methyl-6-[[(1-methylethyl)amino]carbonyl]phenyl]-5-(trifluoromethyl-1H-pyrazole-3-carboxamide To a solution of 1-(3-chloro-2-pyridinyl)-N-[2-methyl-6-[[(1-methylethyl)amino]carbonyl]phenyl]-3-(trifluoromethyl)-1H-pyrazole-5-carboxamide (the product from Step E) (100 mg, 0.21 mmol) in acetonitrile (2 mL) was added 1,8-diazabicyclo[5.4.0]undec-7-ene (DBU, Aldrich, 0.037 mL, 0.26 mmol) and the reaction mixture was stirred at ambient temperature overnight. The reaction mixture was then poured into water (ca. 10 mL) plus 0.5 mL 1N HCl, and then extracted with dichloromethane twice. The organic phase was dried with sodium sulfate and evaporated under reduced pressure to afford 100 mg of crude product as a film. This material was chromatographed by preparative thin layer chromatography on silica using 14% ethyl acetate/dichloromethane as the eluant. The solid that was obtained (52 mg) had a m.p. of 180–182° C. In a separate run using dichloromethane instead of acetonitrile as the reaction solvent, the chromatographed product was subsequently triturated with dichloromethane and hexanes to afford a solid with m.p. 194–195° C.

The proton NMR spectrum at ambient temperatures exhibited very broad, poorly resolved absorptions due to the slow interconversion of conformers. Low temperature was necessary to achieve a highly resolved spectrum, where absorptions for two separate conformers in an approximate 1:1 ratio were apparent:

$^1$H NMR (−50° C., acetone-d$_6$) δ 0.92 (m, 6H), 1.07 (d) plus 1.19 (d) 6H total, 2.2 (s, 3H), 2.4 (s, 3H), 3.9 (m, 1H), 4.18 (m, 1H), 7.3–7.6 (m, 8H), 8.04 (d, 1H), 8.10 (d, 1H), 8.23 (dd, 1H), 8.31 (d, 1H), 8.55 (dd, 1H), 8.64 (d, 1H), 14.1 (br s, 1H), 15.5 (br s, 1H) ppm.

The following Example 2 illustrates an alternative preparation of 1-(3-chloro-2-pyridinyl)-3-(trifluoromethyl)-1H-pyrazole-5-carboxylic acid, which can be used to prepare, for example, N-(3-chloro-2-pyridinyl)-N-[2-methyl-6-[[(1-methylethyl)amino]carbonyl]-phenyl]-5-(trifluoromethyl)-1H-pyrazole-3-carboxamide, by further steps illustrated in Examples 1.

EXAMPLE 2

Preparation of 1 -(3-chloro-2-pyridinyl)-3-(trifluoromethyl)-1H-pyrazole-5-carboxylic acid Step A: Preparation of 3-chloro-2(1H)-pyridinone (2,2,2-trifluoro-1-methylethylidene)hydrazone 1,1,1-Trifluoroacetone (7.80 g, 69.6 mmol) was added to 3-chloro-2(1H)-pyridinone hydrazone (alternatively named (3-chloro-pyridin-2-yl)-hydrazine) (10 g, 69.7 mmol) at 20–25° C. After the addition was complete, the mixture was stirred for about 10 minutes. The solvent was removed under reduced pressure and the mixture partitioned between ethyl acetate (100 mL) and saturated aqueous sodium carbonate solution (100 mL). The organic layer was dried and evaporated. Chromatography on silica gel (eluted with ethyl acetate) gave the product as an off-white solid (11 g, 66% yield), m.p. 64–64.5° C. (after crystallization from ethyl acetate/hexanes).

IR (nujol) ν 1629, 1590, 1518, 1403, 1365, 1309, 1240, 1196, 1158, 1100, 1032, 992, 800 cm$^{-1}$. $^1$H NMR (CDCl$_3$) δ 2.12 (s, 3H), 6.91–6.86 (m, 1H), 7.64–7.61 (m, 1H), 8.33–8.32 (m, 2H). MS m/z 237 (M$^+$).

Step B: Preparation of Ethyl Hydrogen Ethanedioate (3-chloro-2-pyridinyl)(2,2,2-trifluoro-1-methylethylidene) hydrazide (Alternatively Named Ethyl Hydrogen Ethanedioate (3-chloro-2-pyridinyl)(2,2,2-trifluoro-1-methylethylidene)hydrazine)

Triethylamine (20.81 g, 0.206 mol) was added to 3-chloro-2(1H)-pyridinone (2,2,2-trifluoro-1-methylethylidene)hydrazone (i.e. the product of Step A) (32.63 g, 0.137 mol) in dichloromethane (68 mL) at 0° C. Ethyl chlorooxoacetate (18.75 g, 0.137 mol) in dichloromethane (69 mL) was added dropwise to the mixture at 0° C. The mixture was allowed to warm to 25° C. over about 2 hours. The mixture was cooled to 0° C. and a further portion of ethyl chlorooxoacetate (3.75 g, 27.47 mmol) in dichloromethane (14 mL) was added dropwise. After about an additional 1 hour, the mixture was diluted with dichloromethane (about 450 mL), and the mixture was washed with water (2×150 mL). The organic layer was dried and evaporated. Chromatography on silica gel (eluted with 1:1 ethyl acetate-hexanes) gave the product as a solid (42.06 g, 90% yield), m.p. 73.0–73.5° C. (after crystallization from ethyl acetate/hexanes).

IR (nujol) ν 1751, 1720, 1664, 1572, 1417, 1361, 1330, 1202, 1214, 1184, 1137, 1110, 1004, 1043, 1013, 942, 807, 836 cm$^{-1}$. $^1$H NMR (DMSO-d$_6$, 115° C.) 1.19 (t, 3H), 1.72 (br s, 3H), 4.25 (q, 2H), 7.65 (dd, J=8.3, 4.7 Hz, 1H), 8.20 (dd, J=7.6, 1.5 Hz, 1H), 8.55 (d, J=3.6 Hz, 1H). MS m/z 337 (M$^+$).

Step C: Preparation of Ethyl 1-(3-chloro-2-pyridinyl)4,5-dihydro-5-hydroxy-3-(trifluoromethyl)-1H-pyrazole-5-carboxylate Ethyl hydrogen ethanedioate (3-chloro-2-pyridinyl)(2,2,2-trifluoro-1-methyl-ethylidene)hydrazide (i.e. the product of Step B) (5 g, 14.8 mmol) in dimethyl sulfoxide (25 mL)

was added to tetrabutylammonium fluoride hydrate (10 g) in dimethyl sulfoxide (25 mL) over 8 hours. When the addition was complete, the mixture was poured into acetic acid (3.25 g) in water (25 mL). After stirring at 25° C. overnight, the mixture was then extracted with toluene (4×25 mL), and the combined toluene extracts were washed with water (50 mL), dried and evaporated to give a solid. Chromatography on silica gel (eluted with 1:2 ethyl acetate-hexanes) gave the product as a solid (2.91 g, 50% yield, containing about 5% of 3-chloro-2(1H)-pyridinone (2,2,2-trifluoro-1-methylethylidene)hydrazone), m.p. 78–78.5° C. (after recrystallization from ethyl acetate/hexanes).

IR (nujol) ν 3403, 1726, 1618, 1582, 1407, 1320, 1293, 1260, 1217, 1187, 1150, 1122, 1100, 1067, 1013, 873, 829 cm$^{-1}$. $^1$H NMR (CDCl$_3$) δ 1.19 (s, 3H), 3.20 (½ of ABZ pattern, J=18 Hz, 1H), 3.42 (½ of ABZ pattern, J=18 Hz, 1H), 4.24 (q, 2H), 6.94 (dd, J=7.9, 4.9 Hz, 1H), 7.74 (dd, J=7.7, 1.5 Hz, 1H), 8.03 (dd,J=4.7, 1.5 Hz, 1H). MS m/z 319 (M$^+$).

Step D: Preparation of Ethyl 1-(3-chloro-2-pyridinyl)-3-(trifluoromethyl)-1H-pyrazole-5-carboxylate Sulfuric acid (concentrated, 2 drops) was added to ethyl 1-(3-chloro-2-pyridinyl)-4,5-dihydro-5-hydroxy-3-(trifluoromethyl)-1H-pyrazole-5-carboxylate (i.e. the product of Step C) (1 g, 2.96 mmol) in acetic acid (10 mL) and the mixture was warmed to 65° C. for about 1 hour. The mixture was allowed to cool to 25° C. and most of the acetic acid was removed under reduced pressure. The mixture was partitioned between saturated aqueous sodium carbonate solution (100 mL) and ethyl acetate (100 mL). The aqueous layer was further extracted with ethyl acetate (100 mL). The combined organic extracts were dried and evaporated to give the product as an oil (0.66 g, 77% yield).

IR (neat) ν 3147, 2986, 1734J 1577, 1547, 1466, 1420, 1367, 1277, 1236, 1135, 1082, 1031, 973, 842, 802 cm$^{-1}$. $^1$H NMR (CDCl$_3$) δ 1.23 (t, 3H), 4.25 (q, 2H), 7.21 (s, 1H), 7.48 (dd, J=8.1, 4.7 Hz, 1H), 7.94 (dd, J=6.6, 2 Hz, 1H), 8.53 (dd, J=4.7, 1.5 Hz, 1H). MS m/z 319 (M$^+$).

Step E: Preparation of 1-(3-chloro-2-pyridinyl)-3-(trifluoromethyl)-1H-pyrazole-5-carboxylic acid Potassium hydroxide (0.5 g, 85%, 2.28 mmol) in water (1 mL) was added to ethyl 1-(3-chloro-2-pyridinyl)-3-(trifluoromethyl)-1H-pyrazole-5-carboxylate (i.e. the product of Step D) (0.66 g, 2.07 mmol) in ethanol (3 mL). After about 30 minutes, the solvent was removed under reduced pressure, and the mixture was dissolved in water (40 mL). The solution was washed with ethyl acetate (20 mL). The aqueous layer was acidified with concentrated hydrochloric acid and was extracted with ethyl acetate (3×20 mL). The combined extracts were dried and evaporated to give the product as a solid (0.53 g, 93% yield), m.p. 178–179° C. (after crystallization from hexanes-ethyl acetate).

IR (nujol) ν 1711, 1586, 1565, 1550, 1440, 1425, 1292, 1247, 1219, 1170, 1135, 1087, 1059, 1031, 972, 843, 816 cm$^{-1}$.

$^1$H NMR(DMSO-d$_6$) δ 7.61 (s, 1H), 7.77 (m, 1H), 8.30 (d, 1H), 8.60 (s, 1H).

By the procedures described herein together with methods known in the art, the following compounds of Table 1 can be prepared. The following abbreviations are used in the Tables which follow: t means tertiary, s means secondary, n means normal, i means iso, Me means methyl, Et means ethyl, Pr means propyl, i-Pr means isopropyl and Bu means butyl.

TABLE 1

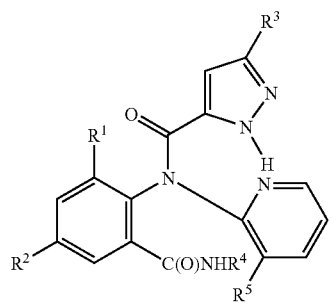

I

| R$^1$ | R$^2$ | R$^3$ | R$^4$ | R$^5$ |
|---|---|---|---|---|
| CH$_3$ | F | CF$_3$ | Me | Cl |
| CH$_3$ | F | CF$_3$ | Et | Cl |
| CH$_3$ | F | CF$_3$ | i-Pr | Cl |
| CH$_3$ | F | CF$_3$ | t-Bu | Cl |
| CH$_3$ | F | CF$_3$ | Me | Br |
| CH$_3$ | F | CF$_3$ | Et | Br |
| CH$_3$ | F | CF$_3$ | i-Pr | Br |
| CH$_3$ | F | CF$_3$ | t-Bu | Br |
| CH$_3$ | F | Cl | Me | Cl |
| CH$_3$ | F | Cl | Et | Cl |
| CH$_3$ | F | Cl | i-Pr | Cl |
| CH$_3$ | F | Cl | t-Bu | Cl |
| CH$_3$ | F | Cl | Me | Br |
| CH$_3$ | F | Cl | Et | Br |
| CH$_3$ | F | Cl | i-Pr | Br |
| CH$_3$ | F | Cl | t-Bu | Br |
| CH$_3$ | F | Br | Me | Cl |
| CH$_3$ | F | Br | Et | Cl |
| CH$_3$ | F | Br | i-Pr | Cl |
| CH$_3$ | F | Br | t-Bu | Cl |
| CH$_3$ | F | Br | Me | Br |
| CH$_3$ | F | Br | Et | Br |
| CH$_3$ | F | Br | i-Pr | Br |
| CH$_3$ | F | Br | t-Bu | Br |
| CH$_3$ | Cl | CF$_3$ | Me | Cl |
| CH$_3$ | Cl | CF$_3$ | Et | Cl |
| CH$_3$ | Cl | CF$_3$ | i-Pr | Cl |
| CH$_3$ | Cl | CF$_3$ | t-Bu | Cl |
| CH$_3$ | Cl | CF$_3$ | Me | Br |
| CH$_3$ | Cl | CF$_3$ | Et | Br |
| CH$_3$ | Cl | CF$_3$ | i-Pr | Br |
| CH$_3$ | Cl | CF$_3$ | t-Bu | Br |
| CH$_3$ | Cl | Cl | Me | Cl |
| CH$_3$ | Cl | Cl | Et | Cl |
| CH$_3$ | Cl | Cl | i-Pr | Cl |
| CH$_3$ | Cl | Cl | t-Bu | Cl |
| CH$_3$ | Cl | Cl | Me | Br |
| CH$_3$ | Cl | Cl | Et | Br |
| CH$_3$ | Cl | Cl | i-Pr | Br |
| CH$_3$ | Cl | Cl | t-Bu | Br |
| CH$_3$ | Cl | Br | Me | Cl |
| CH$_3$ | Cl | Br | Et | Cl |
| CH$_3$ | Cl | Br | i-Pr | Cl |
| CH$_3$ | Cl | Br | t-Bu | Cl |
| CH$_3$ | Cl | Br | Me | Br |
| CH$_3$ | Cl | Br | Et | Br |
| CH$_3$ | Cl | Br | i-Pr | Br |
| CH$_3$ | Cl | Br | t-Bu | Br |
| CH$_3$ | Br | CF$_3$ | Me | Cl |
| CH$_3$ | Br | CF$_3$ | Et | Cl |
| CH$_3$ | Br | CF$_3$ | i-Pr | Cl |
| CH$_3$ | Br | CF$_3$ | t-Bu | Cl |
| CH$_3$ | Br | CF$_3$ | Me | Br |
| CH$_3$ | Br | CF$_3$ | Et | Br |
| CH$_3$ | Br | CF$_3$ | i-Pr | Br |
| CH$_3$ | Br | CF$_3$ | t-Bu | Br |
| CH$_3$ | Br | Cl | Me | Cl |
| CH$_3$ | Br | Cl | Et | Cl |
| CH$_3$ | Br | Cl | i-Pr | Cl |
| CH$_3$ | Br | Cl | t-Bu | Cl |

TABLE 1-continued

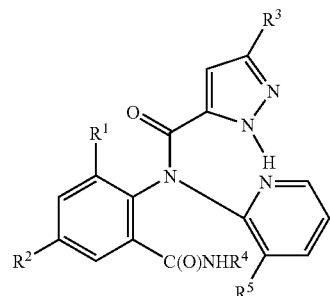

| R¹ | R² | R³ | R⁴ | R⁵ |
|---|---|---|---|---|
| CH₃ | Br | Cl | Me | Br |
| CH₃ | Br | Cl | Et | Br |
| CH₃ | Br | Cl | i-Pr | Br |
| CH₃ | Br | Cl | t-Bu | Br |
| CH₃ | Br | Br | Me | Cl |
| CH₃ | Br | Br | Et | Cl |
| CH₃ | Br | Br | i-Pr | Cl |
| CH₃ | Br | Br | t-Bu | Cl |
| CH₃ | Br | Br | Me | Br |
| CH₃ | Br | Br | Et | Br |
| CH₃ | Br | Br | i-Pr | Br |
| CH₃ | Br | Br | t-Bu | Br |
| CH₃ | I | CF₃ | Me | Cl |
| CH₃ | I | CF₃ | Et | Cl |
| CH₃ | I | CF₃ | i-Pr | Cl |
| CH₃ | I | CF₃ | t-Bu | Cl |
| CH₃ | I | CF₃ | Me | Br |
| CH₃ | I | CF₃ | Et | Br |
| CH₃ | I | CF₃ | i-Pr | Br |
| CH₃ | I | CF₃ | t-Bu | Br |
| CH₃ | I | Cl | Me | Cl |
| CH₃ | I | Cl | Et | Cl |
| CH₃ | I | Cl | i-Pr | Cl |
| CH₃ | I | Cl | t-Bu | Cl |
| CH₃ | I | Cl | Me | Br |
| CH₃ | I | Cl | Et | Br |
| CH₃ | I | Cl | i-Pr | Br |
| CH₃ | I | Cl | t-Bu | Br |
| CH₃ | I | Br | Me | Cl |
| CH₃ | I | Br | Et | Cl |
| CH₃ | I | Br | i-Pr | Cl |
| CH₃ | I | Br | t-Bu | Cl |
| CH₃ | I | Br | Me | Br |
| CH₃ | I | Br | Et | Br |
| CH₃ | I | Br | i-Pr | Br |
| CH₃ | I | Br | t-Bu | Br |
| CH₃ | CF₃ | CF₃ | Me | Cl |
| CH₃ | CF₃ | CF₃ | Et | Cl |
| CH₃ | CF₃ | CF₃ | i-Pr | Cl |
| CH₃ | CF₃ | CF₃ | t-Bu | Cl |
| CH₃ | CF₃ | CF₃ | Me | Br |
| CH₃ | CF₃ | CF₃ | Et | Br |
| CH₃ | CF₃ | CF₃ | i-Pr | Br |
| CH₃ | CF₃ | CF₃ | t-Bu | Br |
| CH₃ | CF₃ | Cl | Me | Cl |
| CH₃ | CF₃ | Cl | Et | Cl |
| CH₃ | CF₃ | Cl | i-Pr | Cl |
| CH₃ | CF₃ | Cl | t-Bu | Cl |
| CH₃ | CF₃ | Cl | Me | Br |
| CH₃ | CF₃ | Cl | Et | Br |
| CH₃ | CF₃ | Cl | i-Pr | Br |
| CH₃ | CF₃ | Cl | t-Bu | Br |
| CH₃ | CF₃ | Br | Me | Cl |
| CH₃ | CF₃ | Br | Et | Cl |
| CH₃ | CF₃ | Br | i-Pr | Cl |
| CH₃ | CF₃ | Br | t-Bu | Cl |
| CH₃ | CF₃ | Br | Me | Br |
| CH₃ | CF₃ | Br | Et | Br |
| CH₃ | CF₃ | Br | i-Pr | Br |
| CH₃ | CF₃ | Br | t-Bu | Br |

TABLE 1-continued

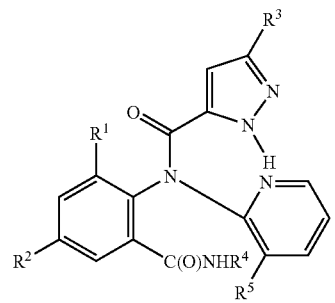

| R¹ | R² | R³ | R⁴ | R⁵ |
|---|---|---|---|---|
| CH₃ | Cl | Cl | n-Pr | Cl |
| CH₃ | Cl | Cl | n-Bu | Cl |
| CH₃ | Cl | Cl | s-Bu | Cl |
| CH₃ | Cl | Cl | i-Bu | Cl |
| Cl | F | CF₃ | Me | Cl |
| Cl | F | CF₃ | Et | Cl |
| Cl | F | CF₃ | i-Pr | Cl |
| Cl | F | CF₃ | t-Bu | Cl |
| Cl | F | CF₃ | Me | Br |
| Cl | F | CF₃ | Et | Br |
| Cl | F | CF₃ | i-Pr | Br |
| Cl | F | CF₃ | t-Bu | Br |
| Cl | F | Cl | Me | Cl |
| Cl | F | Cl | Et | Cl |
| Cl | F | Cl | i-Pr | Cl |
| Cl | F | Cl | t-Bu | Cl |
| Cl | F | Cl | Me | Br |
| Cl | F | Cl | Et | Br |
| Cl | F | Cl | i-Pr | Br |
| Cl | F | Cl | t-Bu | Br |
| Cl | F | Br | Me | Cl |
| Cl | F | Br | Et | Cl |
| Cl | F | Br | i-Pr | Cl |
| Cl | F | Br | t-Bu | Cl |
| Cl | F | Br | Me | Br |
| Cl | F | Br | Et | Br |
| Cl | F | Br | i-Pr | Br |
| Cl | F | Br | t-Bu | Br |
| Cl | Cl | CF₃ | Me | Cl |
| Cl | Cl | CF₃ | Et | Cl |
| Cl | Cl | CF₃ | i-Pr | Cl |
| Cl | Cl | CF₃ | t-Bu | Cl |
| Cl | Cl | CF₃ | Me | Br |
| Cl | Cl | CF₃ | Et | Br |
| Cl | Cl | CF₃ | i-Pr | Br |
| Cl | Cl | CF₃ | t-Bu | Br |
| Cl | Cl | Cl | Me | Cl |
| Cl | Cl | Cl | Et | Cl |
| Cl | Cl | Cl | i-Pr | Cl |
| Cl | Cl | Cl | t-Bu | Cl |
| Cl | Cl | Cl | Me | Br |
| Cl | Cl | Cl | Et | Br |
| Cl | Cl | Cl | i-Pr | Br |
| Cl | Cl | Cl | t-Bu | Br |
| Cl | Cl | Br | Me | Cl |
| Cl | Cl | Br | Et | Cl |
| Cl | Cl | Br | i-Pr | Cl |
| Cl | Cl | Br | t-Bu | Cl |
| Cl | Cl | Br | Me | Br |
| Cl | Cl | Br | Et | Br |
| Cl | Cl | Br | i-Pr | Br |
| Cl | Cl | Br | t-Bu | Br |
| Cl | Br | CF₃ | Me | Cl |
| Cl | Br | CF₃ | Et | Cl |
| Cl | Br | CF₃ | i-Pr | Cl |
| Cl | Br | CF₃ | t-Bu | Cl |
| Cl | Br | CF₃ | Me | Br |
| Cl | Br | CF₃ | Et | Br |
| Cl | Br | CF₃ | i-Pr | Br |
| Cl | Br | CF₃ | t-Bu | Br |

TABLE 1-continued

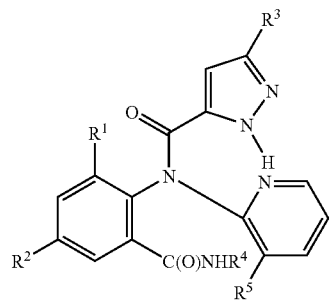

| R¹ | R² | R³ | R⁴ | R⁵ |
|---|---|---|---|---|
| Cl | Br | Cl | Me | Cl |
| Cl | Br | Cl | Et | Cl |
| Cl | Br | Cl | i-Pr | Cl |
| Cl | Br | Cl | t-Bu | Cl |
| CH₃ | H | CF₃ | Me | Cl |
| CH₃ | H | CF₃ | Et | Cl |
| CH₃ | H | CF₃ | i-Pr | Cl |
| CH₃ | H | CF₃ | t-Bu | Cl |
| CH₃ | H | CF₃ | Me | Br |
| CH₃ | H | CF₃ | Et | Br |
| CH₃ | H | CF₃ | i-Pr | Br |
| CH₃ | H | CF₃ | t-Bu | Br |
| CH₃ | H | Cl | Me | Cl |
| CH₃ | H | Cl | Et | Cl |
| CH₃ | H | Cl | i-Pr | Cl |
| CH₃ | H | Cl | t-Bu | Cl |
| CH₃ | H | Cl | Me | Br |
| CH₃ | H | Cl | Et | Br |
| CH₃ | H | Cl | i-Pr | Br |
| CH₃ | H | Cl | t-Bu | Br |
| CH₃ | H | Br | Me | Cl |
| CH₃ | H | Br | Et | Cl |
| CH₃ | H | Br | i-Pr | Cl |
| CH₃ | H | Br | t-Bu | Cl |
| CH₃ | H | Br | Me | Br |
| CH₃ | H | Br | Et | Br |
| CH₃ | H | Br | i-Pr | Br |
| CH₃ | H | Br | t-Bu | Br |
| Cl | Br | Cl | Me | Br |
| Cl | Br | Cl | Et | Br |
| Cl | Br | Cl | i-Pr | Br |
| Cl | Br | Cl | t-Bu | Br |
| Cl | Br | Br | Me | Cl |
| Cl | Br | Br | Et | Cl |
| Cl | Br | Br | i-Pr | Cl |
| Cl | Br | Br | t-Bu | Cl |
| Cl | Br | Br | Me | Br |
| Cl | Br | Br | Et | Br |
| Cl | Br | Br | i-Pr | Br |
| Cl | Br | Br | t-Bu | Br |
| Cl | I | CF₃ | Me | Cl |
| Cl | I | CF₃ | Et | Cl |
| Cl | I | CF₃ | i-Pr | Cl |
| Cl | I | CF₃ | t-Bu | Cl |
| Cl | I | CF₃ | Me | Br |
| Cl | I | CF₃ | Et | Br |
| Cl | I | CF₃ | i-Pr | Br |
| Cl | I | CF₃ | t-Bu | Br |
| Cl | I | Cl | Me | Cl |
| Cl | I | Cl | Et | Cl |
| Cl | I | Cl | i-Pr | Cl |
| Cl | I | Cl | t-Bu | Cl |
| Cl | I | Cl | Me | Br |
| Cl | I | Cl | Et | Br |
| Cl | I | Cl | i-Pr | Br |
| Cl | I | Cl | t-Bu | Br |
| Cl | I | Br | Me | Cl |
| Cl | I | Br | Et | Cl |
| Cl | I | Br | i-Pr | Cl |
| Cl | I | Br | t-Bu | Cl |
| Cl | I | Br | Me | Br |
| Cl | I | Br | Et | Br |
| Cl | I | Br | i-Pr | Br |
| Cl | I | Br | t-Bu | Br |
| Cl | CF₃ | CF₃ | Me | Cl |
| Cl | CF₃ | CF₃ | Et | Cl |
| Cl | CF₃ | CF₃ | i-Pr | Cl |
| Cl | CF₃ | CF₃ | t-Bu | Cl |
| Cl | CF₃ | CF₃ | Me | Br |
| Cl | CF₃ | CF₃ | Et | Br |
| Cl | CF₃ | CF₃ | i-Pr | Br |
| Cl | CF₃ | CF₃ | t-Bu | Br |
| Cl | CF₃ | Cl | Me | Cl |
| Cl | CF₃ | Cl | Et | Cl |
| Cl | CF₃ | Cl | i-Pr | Cl |
| Cl | CF₃ | Cl | t-Bu | Cl |
| Cl | CF₃ | Cl | Me | Br |
| Cl | CF₃ | Cl | Et | Br |
| Cl | CF₃ | Cl | i-Pr | Br |
| Cl | CF₃ | Cl | t-Bu | Br |
| Cl | CF₃ | Br | Me | Cl |
| Cl | CF₃ | Br | Et | Cl |
| Cl | CF₃ | Br | i-Pr | Cl |
| Cl | CF₃ | Br | t-Bu | Cl |
| Cl | CF₃ | Br | Me | Br |
| Cl | CF₃ | Br | Et | Br |
| Cl | CF₃ | Br | i-Pr | Br |
| Cl | CF₃ | Br | t-Bu | Br |
| Cl | Cl | Cl | n-Pr | Cl |
| Cl | Cl | Cl | n-Bu | Cl |
| Cl | Cl | Cl | s-Bu | Cl |
| Cl | Cl | Cl | i-Bu | Cl |
| Br | F | CF₃ | Me | Cl |
| Br | F | CF₃ | Et | Cl |
| Br | F | CF₃ | i-Pr | Cl |
| Br | F | CF₃ | t-Bu | Cl |
| Br | F | CF₃ | Me | Br |
| Br | F | CF₃ | Et | Br |
| Br | F | CF₃ | i-Pr | Br |
| Br | F | CF₃ | t-Bu | Br |
| Br | F | Cl | Me | Cl |
| Br | F | Cl | Et | Cl |
| Br | F | Cl | i-Pr | Cl |
| Br | F | Cl | t-Bu | Cl |
| Br | F | Cl | Me | Br |
| Br | F | Cl | Et | Br |
| Br | F | Cl | i-Pr | Br |
| Br | F | Cl | t-Bu | Br |
| Br | F | Br | Me | Cl |
| Br | F | Br | Et | Cl |
| Br | F | Br | i-Pr | Cl |
| Br | F | Br | t-Bu | Cl |
| Br | F | Br | Me | Br |
| Br | F | Br | Et | Br |
| Br | F | Br | i-Pr | Br |
| Br | F | Br | t-Bu | Br |
| Br | Cl | CF₃ | Me | Cl |
| Br | Cl | CF₃ | Et | Cl |
| Br | Cl | CF₃ | i-Pr | Cl |
| Br | Cl | CF₃ | t-Bu | Cl |

TABLE 1-continued

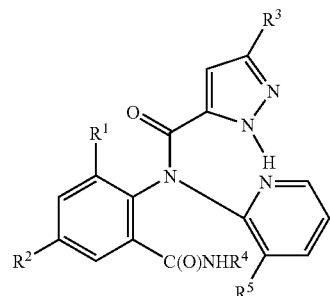

| R¹ | R² | R³ | R⁴ | R⁵ |
|----|----|----|----|----|
| Br | Cl | CF₃ | Me | Br |
| Br | Cl | CF₃ | Et | Br |
| Br | Cl | CF₃ | i-Pr | Br |
| Br | Cl | CF₃ | t-Bu | Br |
| Br | Cl | Cl | Me | Cl |
| Br | Cl | Cl | Et | Cl |
| Br | Cl | Cl | i-Pr | Cl |
| Br | Cl | Cl | t-Bu | Cl |
| Br | Cl | Cl | Me | Br |
| Br | Cl | Cl | Et | Br |
| Br | Cl | Cl | i-Pr | Br |
| Br | Cl | Cl | t-Bu | Br |
| Br | Cl | Br | Me | Cl |
| Br | Cl | Br | Et | Cl |
| Br | Cl | Br | i-Pr | Cl |
| Br | Cl | Br | t-Bu | Cl |
| Br | Cl | Br | Me | Br |
| Br | Cl | Br | Et | Br |
| Br | Cl | Br | i-Pr | Br |
| Br | Cl | Br | t-Bu | Br |
| Br | Br | CF₃ | Me | Cl |
| Br | Br | CF₃ | Et | Cl |
| Br | Br | CF₃ | i-Pr | Cl |
| Br | Br | CF₃ | t-Bu | Cl |
| Br | Br | CF₃ | Me | Br |
| Br | Br | CF₃ | Et | Br |
| Br | Br | CF₃ | i-Pr | Br |
| Br | Br | CF₃ | t-Bu | Br |
| Br | Br | Cl | Me | Cl |
| Br | Br | Cl | Et | Cl |
| Br | Br | Cl | i-Pr | Cl |
| Br | Br | Cl | t-Bu | Cl |
| Br | Br | Cl | Me | Br |
| Br | Br | Cl | Et | Br |
| Br | Br | Cl | i-Pr | Br |
| Br | Br | Cl | t-Bu | Br |
| Br | Br | Br | Me | Cl |
| Br | Br | Br | Et | Cl |
| Br | Br | Br | i-Pr | Cl |
| Br | Br | Br | t-Bu | Cl |
| Br | Br | Br | Me | Br |
| Br | Br | Br | Et | Br |
| Br | Br | Br | i-Pr | Br |
| Br | Br | Br | t-Bu | Br |
| Br | I | CF₃ | Me | Cl |
| Br | I | CF₃ | Et | Cl |
| Br | I | CF₃ | i-Pr | Cl |
| Br | I | CF₃ | t-Bu | Cl |
| Br | I | CF₃ | Me | Br |
| Br | I | CF₃ | Et | Br |
| Br | I | CF₃ | i-Pr | Br |
| Br | I | CF₃ | t-Bu | Br |
| Br | I | Cl | Me | Cl |
| Br | I | Cl | Et | Cl |
| Br | I | Cl | i-Pr | Cl |
| Br | I | Cl | t-Bu | Cl |
| Br | I | Cl | Me | Br |
| Br | I | Cl | Et | Br |
| Br | I | Cl | i-Pr | Br |
| Br | I | Cl | t-Bu | Br |

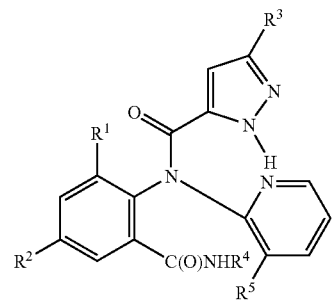

| R¹ | R² | R³ | R⁴ | R⁵ |
|----|----|----|----|----|
| Br | I | Br | Me | Cl |
| Br | I | Br | Et | Cl |
| Br | I | Br | i-Pr | Cl |
| Br | I | Br | t-Bu | Cl |
| Br | I | Br | Me | Br |
| Br | I | Br | Et | Br |
| Br | I | Br | i-Pr | Br |
| Br | I | Br | t-Bu | Br |
| Br | CF₃ | CF₃ | Me | Cl |
| Br | CF₃ | CF₃ | Et | Cl |
| Br | CF₃ | CF₃ | i-Pr | Cl |
| Br | CF₃ | CF₃ | t-Bu | Cl |
| Br | CF₃ | CF₃ | Me | Br |
| Br | CF₃ | CF₃ | Et | Br |
| Br | CF₃ | CF₃ | i-Pr | Br |
| Br | CF₃ | CF₃ | t-Bu | Br |
| Br | CF₃ | Cl | Me | Cl |
| Br | CF₃ | Cl | Et | Cl |
| Br | CF₃ | Cl | i-Pr | Cl |
| Br | CF₃ | Cl | t-Bu | Cl |
| Br | CF₃ | Cl | Me | Br |
| Br | CF₃ | Cl | Et | Br |
| Br | CF₃ | Cl | i-Pr | Br |
| Br | CF₃ | Cl | t-Bu | Br |
| Br | CF₃ | Br | Me | Cl |
| Br | CF₃ | Br | Et | Cl |
| Br | CF₃ | Br | i-Pr | Cl |
| Br | CF₃ | Br | t-Bu | Cl |
| Br | CF₃ | Br | Me | Br |
| Br | CF₃ | Br | Et | Br |
| Br | CF₃ | Br | i-Pr | Br |
| Br | CF₃ | Br | t-Bu | Br |
| Cl | H | CF₃ | Me | Cl |
| Cl | H | CF₃ | Et | Cl |
| Cl | H | CF₃ | i-Pr | Cl |
| Cl | H | CF₃ | t-Bu | Cl |
| Cl | H | CF₃ | Me | Br |
| Cl | H | CF₃ | Et | Br |
| Cl | H | CF₃ | i-Pr | Br |
| Cl | H | CF₃ | t-Bu | Br |
| Cl | H | Cl | Me | Cl |
| Cl | H | Cl | Et | Cl |
| Cl | H | Cl | i-Pr | Cl |
| Cl | H | Cl | t-Bu | Cl |
| Cl | H | Cl | Me | Br |
| Cl | H | Cl | Et | Br |
| Cl | H | Cl | i-Pr | Br |
| Cl | H | Cl | t-Bu | Br |
| Cl | H | Br | Me | Cl |
| Cl | H | Br | Et | Cl |
| Cl | H | Br | i-Pr | Cl |
| Cl | H | Br | t-Bu | Cl |
| Cl | H | Br | Me | Br |
| Cl | H | Br | Et | Br |
| Cl | H | Br | i-Pr | Br |
| Cl | H | Br | t-Bu | Br |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Pub. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxy-ethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, propylene carbonate, dibasic esters, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook,* 4th Ed., McGraw-Hill, New York, 1963, pages 8–57 and following, and PCT Publication WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modem Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120–133. See also U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook,* 8th Ed, Blackwell Scientific Publications, Oxford, 1989.

In the following Examples, all percentages are by weight and all formulations are prepared in conventional ways. Compound numbers refer to compounds in Index Table A.

| Example A | |
|---|---|
| Wettable Powder | |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |
| Example B | |
| Granule | |
| Compound 1 | 10.0% |
| attapulgite granules (low volatile matter, 0.71/0.30 mm; U.S.S. No. 25–50 sieves) | 90.0%. |
| Example C | |
| Extruded Pellet | |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

-continued

Example D

Emulsifiable Concentrate

| | |
|---|---|
| Compound 1 | 20.0% |
| blend of oil soluble sulfonates and polyoxyethylene ethers | 10.0% |
| isophorone | 70.0%. |

Example E

Granule

| | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity against a spectrum of foliar and soil inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests. Compounds of this invention display activity against economically important agronomic, forestry, greenhouse, nursery, ornamental food and fiber product, stored product, domestic structure, household, and public and animal health pests, such as: larvae of the order Lepidoptera including fall and beet armyworm and other *Spodoptera* spp., tobacco budworm, corn earworm and other *Heliothis* spp., European corn borer, navel orangeworm, stalk/stem borers and other pyralids, cabbage and soybean loopers and other loopers, codling moth, grape berry moth and other tortricids, black cutworm, spotted cutworm, other cutworms and other noctuids, diamondback moth, velvetbean caterpillar, green cloverworm, pink bollworm, gypsy moth, and spruce budworm; foliar feeding larvae and adults of the order Coleoptera including Colorado potato beetle, Mexican bean beetle, flea beetles, Japanese beetles, and other leaf beetles, boll weevil, rice water weevil, granary weevil, rice weevil and other weevil pests, and soil inhabiting insects such as Western corn rootworm and other *Diabrotica* spp., Japanese beetle, European chafer and other coleopteran grubs, and wireworms; adults and larvae of the orders Hemiptera and Homoptera including tarnished plant bug and other plant bugs (Miridae), aster leafhopper and other leafhoppers (Cicadellidae), rice planthopper, brown planthopper, and other planthoppers (Fulgoroidea), psylids, whiteflies (Aleurodidae), aphids (Aphidae), scales (Coccidae and Diaspididae), lace bugs (Tingidae), stink bugs (Pentatomidae), cinch bugs and other seed bugs (Lygaeidae), cicadas (Cicadidae), spittlebugs (Cercopids), squash bugs (Coreidae), red bugs and cotton stainers (Pyrrhocoridae); adults and larvae of the order acari (mites) including European red mite, two spotted spider mite, rust mites, McDaniel mite, and other foliar feeding mites; adults and immatures of the order Orthoptera including grasshoppers; adults and immatures of the order Diptera including leafminers, midges, fruit flies (Tephritidae), and soil maggots; adults and immatures of the order Thysanoptera including onion thrips and other foliar feeding thrips; insect pests of the order Hymenoptera including carpenter ants, bees, hornets, and wasps; insect pests of the order Diptera including house flies, stable flies, face flies, horn flies, blow flies, and other muscoid fly pests, horse flies, deer flies and other Brachycera, mosquitoes, black flies, biting midges, sand flies, sciarids, and other Nematocera; insect pests of the order Orthoptera including cockroaches and crickets; insect pests of the order Isoptera including the Eastern subterranean termite and other termites; insect pests of the order Mallophaga and Anoplura including the head louse, body louse, chicken head louse and other sucking and chewing parasitic lice that attack man and animals; insect pests of the order Siphonoptera including the cat flea, dog flea and other fleas. Compounds of the invention show particularly high activity against pests in the order Lepidoptera (e.g., *Alabama argillacea* Hübner (cotton leaf worm), *Archips argyrospila* Walker (fruit tree leaf roller), *A. rosana* L. (European leaf roller) and other *Archips* species, *Chilo suppressalis* Walker (rice stem borer), *Cnaphalocrosis medinalis* Guenee (rice leaf roller), *Cydia pomonella* L. (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* L. (large white butterfly), *Pieris rapae* L. (small white butterfly), *Plutella xylostella* L. (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). These compounds also have activity on members from the order Homoptera including: *Aphis fabae* Scopoli (black bean aphid), *Aphis gossypii* Glover (cotton aphid, melon aphid), *Diuraphis noxia* Kurdjumov/Mordvilko (Russian wheat aphid), *Myzus persicae* Sulzer (green peach aphid), *Sitobion avenae* Fabricius (English grain aphid), *Bemisia tabaci* Gennadius (tobacco whitefly, sweet potato whitefly), and *Bemisia argentifolli* Bellows & Perring (silverleaf whitefly) and also the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus the present invention also pertains to a composition comprising a biologically effective amount of a compound of Formula 1 and an effective amount of at least one additional biologically active compound or agent and can further comprise at least one of a surfactant, a solid diluent or a liquid diluent. Examples of such biologically active compounds or agents with which compounds of this invention can be formulated are: insecticides such as abamectin, acephate, acetamiprid, amidoflumet (S-1955), avermectin, azadirachtin, azinphosmethyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl pyriproxyfen, rotenone, spinosad, spiromesifm (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC375839), myclobutanil, neo-asozin (ferric methanearsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi. Compounds of this invention and compositions thereof can be applied to plants genetically transformed to express proteins toxic to invertebrate pests (such as Bacillus thuringiensis toxin). The effect of the exogenously applied invertebrate pest control compounds of this invention may be synergistic with the expressed toxin proteins.

A general reference for these agricultural protectants is *The Pesticide Manual, 12th Edition*, C. D. S. Tomlin, Ed., British Crop Protection Council, Farnham, Surrey, U.K., 2000.

Of note are compositions comprising (addition to the Formula I component and any surfactant and/or diluent) at least one additional biologically active compound or agent selected from the group consisting of abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoplrene, methoxychlor, monocrotophos, methoxyfenozide, nithiazin, novaluron, oxamyl parathion, parathion-methyl, permethrin, phorate, phosalone, phosmet, phosphamidon, pirimicarb, profenofos, pymetrozine, pyridalyl pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben, tebufenpyrad, *Bacillus thuringiensis* including ssp. *aizawai* and *kurstaki, Bacillus thuringiensis* delta endotoxin, baculovirus, and entomopathogenic bacteria, virus and fungi.

Preferred insecticides and acaricides for mixing with compounds of this invention include pyrethroids such as cypermethrin, cyhalotnin, cyfluthrin and beta-cyfluthrin, esfenvalerate, fenvalerate and tralomethrin; carbamates such as fenothicarb, methomyl oxamyl and thiodicarb; neonicotinoids such as clothianidin, imidacloprid and thiacloprid, neuronal sodium channel blockers such as indoxacarb, insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron, juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other arthropodicides having a similar spectrum of control but a different mode of action will be particularly advantageous for resistance management.

Arthropod pests are controlled and protection of agronomnic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar- and soil-inhabiting arthropods and protection of agronomic and/or nonagronomic crops, comprising contacting the arthropods or their environment with an arthropodically effective amount of one or more compounds of the invention, or with a composition comprising at least one such compound. A preferred method of contact is by spraying. Alternatively, a granular composition comprising a compound of the invention can be applied to the plant foliage or the soil. Compounds of this invention are effective in delivery through plant uptake by contacting the plant with a composition comprising a compound of this invention applied as a soil drench of a liquid formulation, a granular formulation to the soil, a nursery box treatment or a dip of transplants. Other methods of contact include application of a compound or a composition of the invention by direct and residual sprays, aerial sprays, seed coats, microencapsulations, systemic uptake, baits, eartags, boluses, foggers, fumigants, aerosols, dusts and many others.

The compounds of this invention can be incorporated into baits that are consumed by the arthropods or within devices such as traps and the like. Granules or baits comprising between 0.01–5% active ingredient, 0.05–10% moisture retaining agent(s) and 40–99% vegetable flour are effective in controlling soil insects at very low application rates, particularly at doses of active ingredient that are lethal by ingestion rather than by direct external contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required.

The following Tests in the Biological Examples of the Invention demonstrate the control efficacy of compounds of this invention on specific pests. "Control efficacy" represents inhibition of arthropod development (including mortality) that causes significantly reduced feeding. The pest control protection afforded by the compounds is not limited, however, to these species. See Index Table A for compound descriptions. The following abbreviations are used in the Index Table which follows: t is tertiary, n is normal, i is iso, s is secondary, Me is methyl, Et is ethyl, Pr is propyl and Bu is butyl; accordingly i-Pr is isopropyl, s-Bu is secondary butyl etc. The abbreviation "Ex." stands for "Example" and is followed by a number indicating in which example the compound is prepared.

INDEX TABLE A

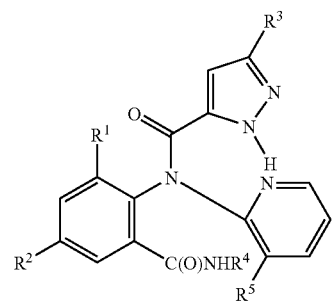

| Compound | R$^1$ | R$^2$ | R$^3$ | R$^4$ | R$^5$ | m.p. (° C.) |
|---|---|---|---|---|---|---|
| 1 (Ex. 1) | Me | H | CF$_3$ | i-Pr | Cl | 194–195 |
| 2 | Me | Br | CF$_3$ | i-Pr | Cl | 168–170 |
| 3 | Me | Cl | Br | i-Pr | Cl | 180–181 |
| 4 | Me | Cl | CF$_3$ | i-Pr | Cl | 173–176 |

BIOLOGICAL EXAMPLES OF THE INVENTION

Test A

For evaluating control of diamondback moth (*Plutella xylostella*) the test unit consisted of a small open container with a 12–14-day-old radish plant inside. This was pre-infested with 10–15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 250 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided excellent levels of plant protection (10% orless feeding damage): 1, 3 and 4.

Test B

For evaluating control of fall armyworm (*Spodoptera frugiperda*) the test unit consisted of a small open container with a 4–5-day-old corn (maize) plant inside. This was pre-infested (using a core sampler) with 10–15 1-day-old larvae on a piece of insect diet.

Test compounds were formulated and sprayed at 250 ppm as described for Test A. The applications were replicated three times. After spraying, the test units were maintained in a growth chamber and then visually rated as described for Test A.

Of the compounds tested, the following provided excellent levels of plant protection (10% or less feeding damage): 1,2,3 and 4.

Test C

For evaluating control of tobacco budworm (*Heliothis virescens*) the test unit consisted of a small open container with a 6–7 day old cotton plant inside. This was pre-infested (using a core sampler) with 8 2-day-old larvae on a piece of insect diet.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (10% or less feeding damage): 1, 2, 3 and 4.

Test D

For evaluating control of beet armyworm (*Spodoptera exigua*) the test unit consisted of a small open container with a 4–5-day-old corn plant inside. This was pre-infested (using a core sampler) with 10–15 1-day-old larvae on a piece of insect diet.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (10% or less feeding damage): 1, 3 and 4.

What is claimed is:

1. A compound of Formula I, its N-oxide or an agriculturally suitable salt of the compound

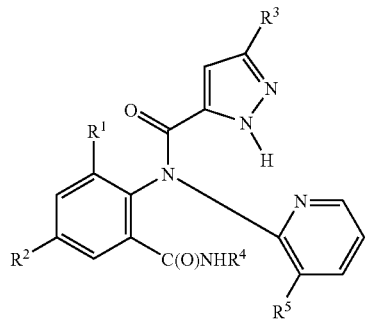

I wherein
$R^1$ and $R^2$ are each independently H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, or $C_3$–$C_6$ trialkylsilyl;

$R^3$ is H, $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl or $C_2$–$C_4$ alkoxycarbonyl;

$R^4$ is H; $C_1$–$C_6$ alkyl, $C_2$–$C_6$ alkenyl, $C_2$–$C_6$ alkynyl, $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_2$–$C_6$ alkoxycarbonyl, $C_2$–$C_6$ alkylcarbonyl, $C_3$–$C_6$ trialkylsilyl, phenyl and phenoxy each phenyl and phenoxy optionally substituted with from one to three substituents independently selected from $R^7$;

$R^5$ is H, $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $CO_2H$, $CONH_2$, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_1$–$C_4$ alkylamino, $C_2$–$C_8$ dialkylamino, $C_3$–$C_6$ cycloalkylamino, $C_2$–$C_6$ alkylcarbonyl, $C_2$–$C_6$ alkoxycarbonyl, $C_2$–$C_6$ alkylaminocarbonyl, $C_3$–$C_8$ dialkylaminocarbonyl, or $C_3$–$C_6$ trialkylsilyl; and each $R^7$ is $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl.

2. A compound of claim 1 wherein
$R^1$ is $C_1$–$C_3$ alkyl, $CF_3$, $OCF_3$, $OCHF_2$, $S(O)_pCF_3$, $S(O)_pCHF_2$ or halogen;
$R^2$ is H, halogen, $C_1$–$C_3$ alkyl or $C_1$–$C_3$ haloalkyl;
$R^3$ is halogen or $CF_3$;
$R^4$ is $C_1$–$C_4$ alkyl optionally substituted with halogen, CN, $OCH_3$, or $S(O)_pCH_3$;
$R^5$ is halogen, $C_1$–$C_4$ alkyl, $C_1$–$C_4$ haloalkyl or $C_1$–$C_4$ haloalkoxy; and
p is 0, 1 or 2.

3. A compound of claim 2 wherein
$R^1$ is $CH_3$, Cl or Br;
$R^2$ is H, F, Cl, Br, I or $CF_3$;
$R^3$ is $CF_3$, Cl or Br;
$R^4$ is $C_2C_4$ alkyl; and
$R^5$ is Cl or Br.

4. A compound of claim 3 wherein
N-(3-chloro-2-pyridinyl)-N-[2-methyl-6-[[(1-methylethyl)amino]carbonyl]phenyl]-5-(trifluoromethyl)-1H-pyrazole-3-carboxamide;

3-bromo-N-(4-chloro-2-methyl)-6-[[(1-methylethyl)amino]carbonyl]phenyl]-N-(3-chloro-2-pyridinyl)-1H-pyrazole-5-carboxamide; or N-[4-chloro-2-methyl -6-[[(1-methylethyl)amino]carbonyl]phenyl]-N-(3-chloro-2-pyridinyl)-3-(trifluoromethyl)-1H-pyrazole-5-carboxamide.

5. An arthropodicidal composition comprising an arthropodicidally effective amount of a compound of claim 1 and at least one additional component selected from the group consisting of surfactants, solid diluents and liquid diluents.

6. A method for controlling arthropods comprising contacting the arthropods or their environment with an arthropodically effective amount of a compound of claim 1.

* * * * *